(12) United States Patent
Lin et al.

(10) Patent No.: US 10,092,530 B2
(45) Date of Patent: Oct. 9, 2018

(54) METHOD FOR INHIBITING MELANOGENESIS AND PROMOTING COLLAGEN PRODUCTION AND WOUND HEALING

(71) Applicant: TCI Co., Ltd, Taipei (TW)

(72) Inventors: Yung-Hsiang Lin, Taipei (TW); Hsiang-Ling Su, Taipei (TW)

(73) Assignee: TCI CO., LTD, Taipei (TW)

( * ) Notice: Subject to any disclaimer, the term of this patent is extended or adjusted under 35 U.S.C. 154(b) by 97 days.

(21) Appl. No.: 15/229,076

(22) Filed: Aug. 4, 2016

(65) Prior Publication Data

US 2017/0079941 A1    Mar. 23, 2017

(30) Foreign Application Priority Data

Aug. 6, 2015 (TW) .............................. 104125700 A

(51) Int. Cl.
| | | |
|---|---|---|
| *A61K 31/19* | (2006.01) | |
| *A61K 8/365* | (2006.01) | |
| *A61Q 19/02* | (2006.01) | |
| *A61Q 19/08* | (2006.01) | |
| *A61K 36/28* | (2006.01) | |
| *C12P 7/42* | (2006.01) | |

(52) U.S. Cl.
CPC .............. *A61K 31/19* (2013.01); *A61K 8/365* (2013.01); *A61K 36/28* (2013.01); *A61Q 19/02* (2013.01); *A61Q 19/08* (2013.01); *C12P 7/42* (2013.01); *A61K 2236/11* (2013.01); *A61K 2236/33* (2013.01)

(58) Field of Classification Search
CPC ........ A61Q 19/08; A61Q 19/02; A61K 8/365; A61K 2236/33; A61K 2236/11; A61K 31/19; A61K 36/28; C12P 7/42
See application file for complete search history.

(56) References Cited

FOREIGN PATENT DOCUMENTS

JP    20001316240 A    * 11/2001

OTHER PUBLICATIONS

JP 20001316240-A, English Translation.*

* cited by examiner

*Primary Examiner* — Angela C Brown-Pettigrew
(74) *Attorney, Agent, or Firm* — WPAT, PC

(57) ABSTRACT

The present invention provides a method for inhibiting melanogenesis, promoting collagen production, and promoting wound healing in the skin of a subject in need thereof, comprising administering to the subject an effective amount of a compound represented by formula (I). The compound of the present invention can inhibit melanin formation, promote collagen production and facilitate wound repair. Therefore, the compound can be utilized to manufacture compositions for skin whitening, anti-aging, and wound healing. The present invention also provides a method of preparing a compound of formula (I).

5 Claims, 15 Drawing Sheets

METHOD FOR INHIBITING MELANOGENESIS AND PROMOTING COLLAGEN PRODUCTION AND WOUND HEALING

CROSS-REFERENCE TO RELATED APPLICATION

This application claims priority of Taiwan patent application No. 104125700, filed on Aug. 6, 2015, the content of which is incorporated herein in its entirety by reference.

BACKGROUND OF THE INVENTION

1. Field of the Invention

The present invention relates to compositions and a method for improving skin health. Particularly, the present invention provides compositions and a method for inhibiting melanogenesis and promoting collagen production and wound healing in the skin.

2. The Prior Art

Melanin is produced via an enzymatic reaction of tyrosinase from tyrosine to DOPA (3,4-dihydroxyphenylalanine) in melanocytes of the skin, or it is produced via a non-enzymatic oxidation reaction. Considering skin pigmentation, such as spots and freckles, it is found that abnormal secretion of hormones or overexposure to UV radiation stimulates melanin overproduction and deposition in the skin.

In order to achieve skin whitening, medical scientists in the related field utilize whitening agents or skin-whitening cosmetics along with L-ascorbic acid and salts thereof, kojic acid, arbutin, or hydroquinone to formulate remedies for treating or reducing spots or freckles resulted from hypermelanogenesis. However, during clinical research, medical scientists have found the drawbacks of poor stability or solubility of these formulations. Besides, the effects of these formulations on reducing or removing melanin are unsatisfactory. When the concentrations of L-ascorbic acid or kojic acid are elevated in the formulations to enhance the skin whitening effects, there would be safety issues.

In view of the facts mentioned above, the inventors of the present application have carried out a tremendous amount of experiments and developed compositions and a method for inhibiting melanogenesis and promoting collagen production and wound healing.

SUMMARY OF THE INVENTION

In one aspect, the present invention provides a method for inhibiting melanogenesis, promoting collagen production, and promoting wound healing in the skin of a subject in need thereof, comprising administering to the subject an effective amount of a compound represented by formula (I):

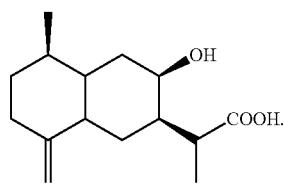

(I)

The compound of formula (I) is distinguished from the tyrosinase inhibitor or general melanogenesis inhibitors in that it not only inhibits melanogenesis but also promotes collagen production and wound healing. In one embodiment of the present invention, the compound exhibits high activities, particularly in human dermal fibroblasts, to inhibits gene expression of microphthalmia-associated transcription factor (MITF) and gene expression of matrix metalloproteinase 9 (MMP-9), and thus the compound inhibits melanin formation and promotes collagen production.

In one preferred embodiment of the present invention, the compound at a concentration of between 8 ng/ml and 18 ng/ml inhibits gene expression of MMP-9 in human dermal fibroblasts by an average of at least 50% and enhances collagen secretion in human dermal fibroblasts by at least 20%.

In another preferred embodiment of the present invention, the compound at a concentration of between 8 ng/ml and 18 ng/ml inhibits gene expression of MITF, a master regulator of melanocyte development, in human dermal fibroblasts by an average of at least 40% and reduces melanin content in mouse melanoma cells by at least 20%.

In another preferred embodiment of the present invention, the compound at a concentration of between 8 ng/ml and 18 ng/ml facilitates repair and closure of a wound area of human dermal fibroblasts, resulting in a 1.21 to 1.4 fold increase in the percentage of wound repair/closure.

In another aspect, the present invention provides a composition for inhibiting melanogenesis and promoting collagen production and wound healing in the skin of a subject in need thereof, comprising a pharmaceutically acceptable carrier and an effective amount of a compound of formula (I).

In one embodiment of the present invention, the compound of formula (I) in the composition is at a concentration of between 8 ng/ml and 18 ng/ml. The composition is in a form selected from a group consisting of suspensions, solutions, emulsions, ointments, lotions, creams, gels, capsules, and powders; the composition further comprises hydroquinone, salicylic acid, an alpha hydroxy acid, hyaluronic acid, and any combinations thereof; and the composition is administered topically or orally.

One further aspect of the present invention provides a method of preparing a compound of formula (I), comprising the steps of: (S1) preparing an explant of *Saussurea involucrate*; (S2) obtaining a callus from the explant of step (S1) and preparing a liquid culture of the callus; (S3) processing the liquid culture of the callus to obtain a biomass of the callus and preparing a ground biomass therefrom; (S4) carrying out a solvent extraction of the ground biomass to obtain at least a supernatant; and (S5) isolating the compound of formula (I) from the supernatant by column chromatography.

In one preferred embodiment of the present invention, the explant of *Saussurea involucrate* of step (S1) is prepared by culturing a young leaf of a *Saussurea involucrate* plant, and the solvent extraction of step (S4) is carried out with 50%-100% ethanol.

The compound of the present invention can inhibit melanogenesis and promote collagen production and wound healing. Therefore, the compound can be utilized in skin care products, cosmetics, wound dressings, pharmaceutical compositions, or food for skin whitening, anti-aging, and wound healing. Also, a method for inhibiting melanogenesis, promoting collagen production and wound healing by using the compound can improve skin health of a subject in need.

The present invention is further explained in the following drawings and examples. It is understood that the examples given below do not limit the scope of the invention, and it will be evident to those skilled in the art that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Definition

The data provided in the present invention represent approximated, experimental values that may vary within a range of ±20%, preferably ±10%, and most preferably ±5%.

The method of preparing the compound of the present invention and the effects of the compound, including inhibition of melanogenesis and promotion of collagen production and wound healing, are described in detail in the following examples along with the drawings.

*Saussurea involucrata* is a species mainly grows in alpine areas of China, such as Xinjiang, Qinghai, Gansu, Yunnan and Tibet. It is usually found between rocks or along cliffs near the snow line at an altitude of 2,400 m to 4,100 m. Because *S. involucrate* is rich in bioactive ingredients, nutrients and minerals, it is comprehensively studied by researchers around the world.

The compound of the present invention can be isolated from *S. involucrate,* and it exhibits activities to inhibit melanogenesis and promote collagen production and wound healing. The compound is represented by formula (I):

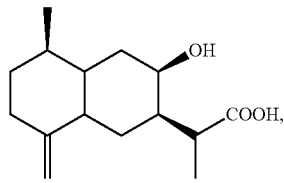

which has the chemical structure of sesquiterpenoid derivatives.

Methods and Materials

Preparation the Compound of Formula (I)

Figure 1:
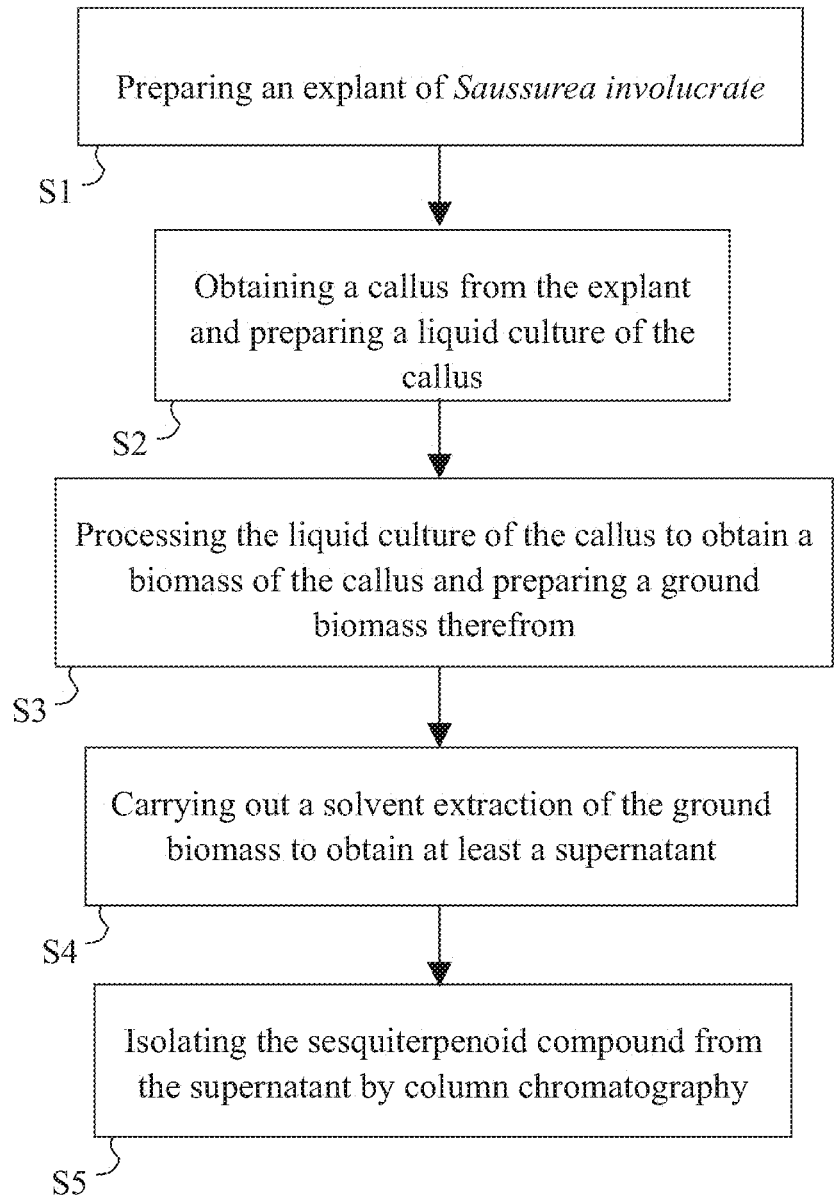
FIG. 1 is a flowchart illustrating preparation of the compound of formula (I) of the present invention.

A method to prepare the compound of the present invention is described, based on which technicians in the related field can obtain the compound unambiguously. FIG. 1 is a flowchart illustrating preparation of the compound of the present invention. As shown in FIG. 1, the method of preparing the compound comprises five major steps:
(S1) preparing an explant of S. involucrate;
(S2) obtaining a callus from the explant of step (S1) and preparing a liquid culture of the callus;
(S3) processing the liquid culture of the callus to obtain a biomass of the callus and preparing a ground biomass therefrom;
(S4) carrying out a solvent extraction of the ground biomass to obtain at least a supernatant; and
(S5) isolating the sesquiterpenoid compound from the supernatant by column chromatography.

Furthermore, the above step (S1) comprises the following substeps:
(S11) obtaining at least one young leaf from a plant of S. involucrate and cutting the at least one young leaf into a plurality of leaf segments;
(S12) rinsing the plurality of leaf segments with bleach (1.5-2% NaClO) for 10 minutes and then washing the plurality of leaf segments with sterile water for 3 minutes;
(S13) inoculating the plurality of leaf segments onto a solid culture medium, which is a MS medium;
(S14) keeping the solid culture medium with the plurality of leaf segments on it in a dark environment and incubating the plurality of leaf segments in the dark at temperatures from 18° C. to 30° C. for five weeks to produce explants of S. involucrate.

In addition, the above step (S2) comprises the following substeps:
(S21) taking out the plurality of leaf segments from the solid culture medium of step (S14) and isolating at least one callus tissue from the plurality of leaf segments;
(S22) mashing the callus tissue and transferring it, with sterilized forceps, into a flask prefilled with 100 ml MS liquid medium;
(S23) keeping the flask with the callus tissue in it in a dark environment and incubating the callus tissue at 25° C. with shaking at 150 rpm for 48 hours to produce a liquid culture of the callus tissue.

Besides, the above step (S3) comprises the following substeps:
(S31) transferring the liquid culture of the callus tissue of step (S23) to a bioreactor system (BTF-A10L, Biotop, Taiwan) for a production test process to obtain a biomass of the callus tissue;

(S32) lyophilizing the biomass of step (S31) to produce a lyophilized biomass;

(S33) grinding the lyophilized biomass to produce a ground biomass.

Figure 2:
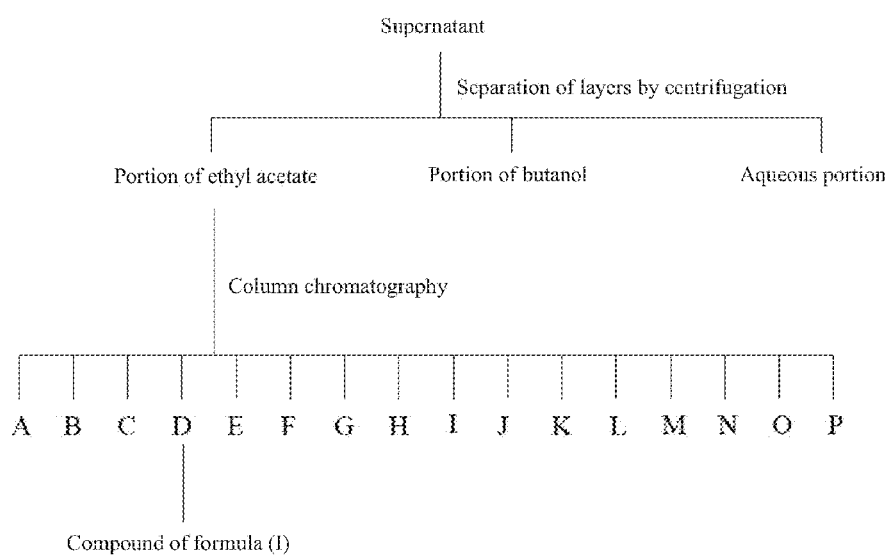
FIG. 2 is a flowchart illustrating isolation of the compound of formula (I) of the present invention from a supernatant of a S. involucrate extract using column chromatography.
Figure 3A:
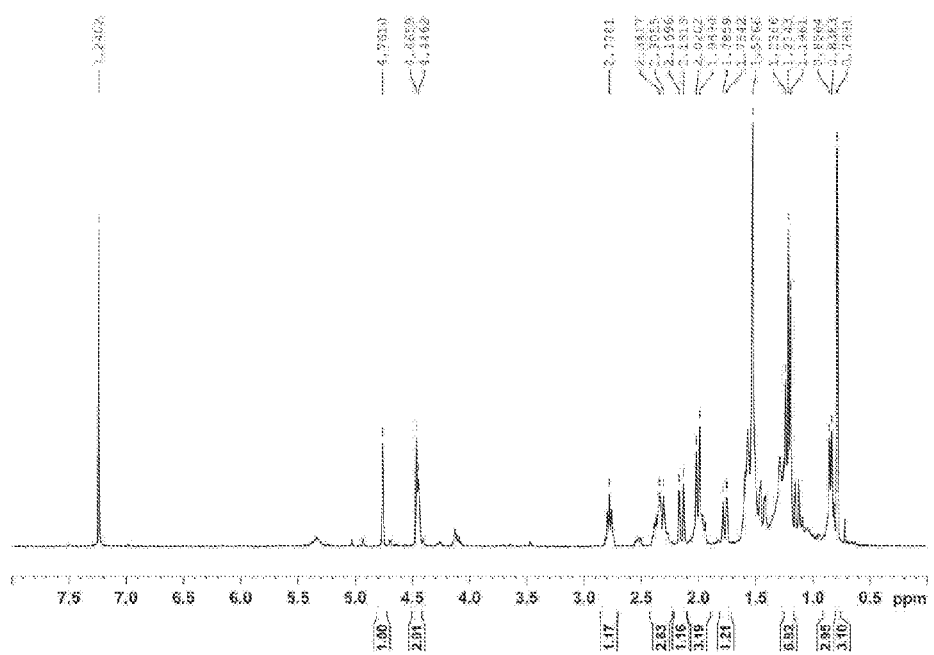
FIG. 3A shows the $^1$H-NMR spectrum for the compound of formula (I)
Figure 3B:
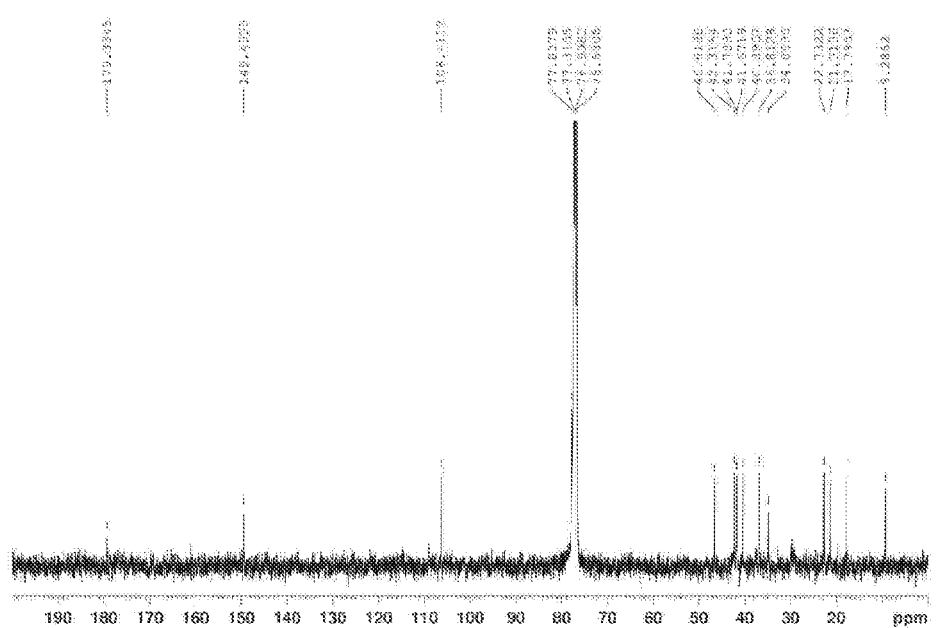
FIG. 3B shows the $^{13}$C-NMR spectrum for the compound of formula (I)
Figure 3C:
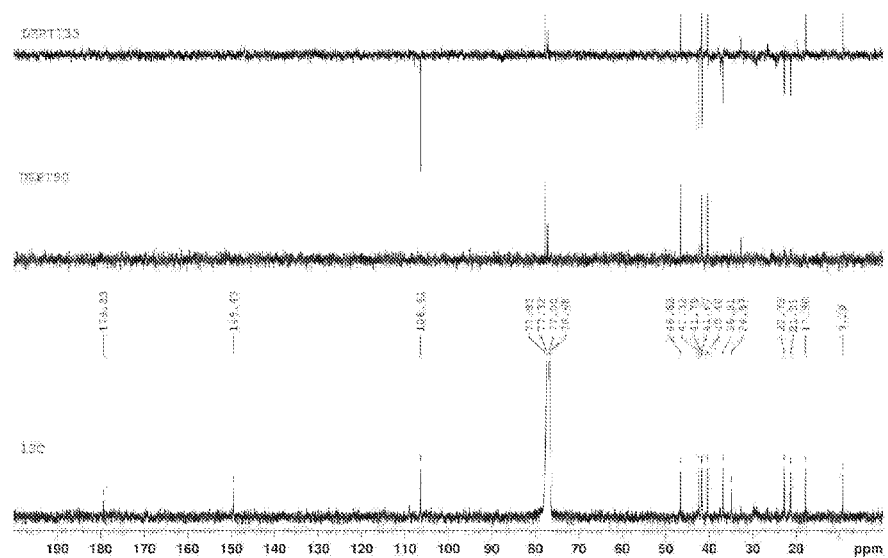
FIG. 3C shows the DEPT spectrum for the compound of formula (I)
Figure 3D:
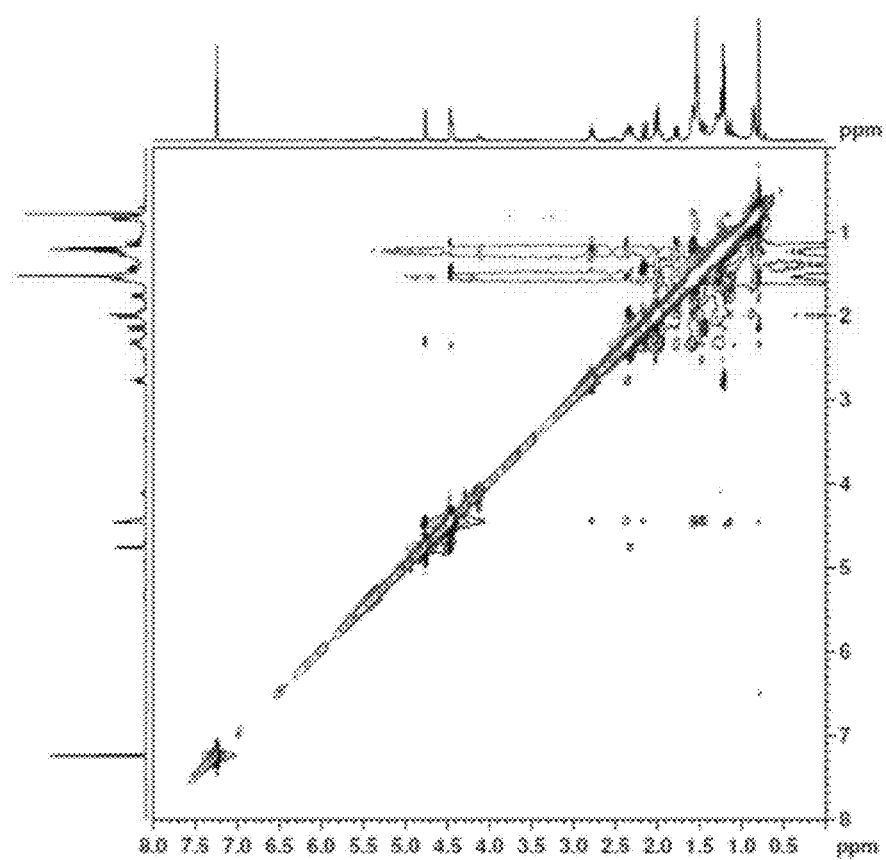
FIG. 3D shows the NOESY spectrum for the compound of formula (I)
Figure 3E:
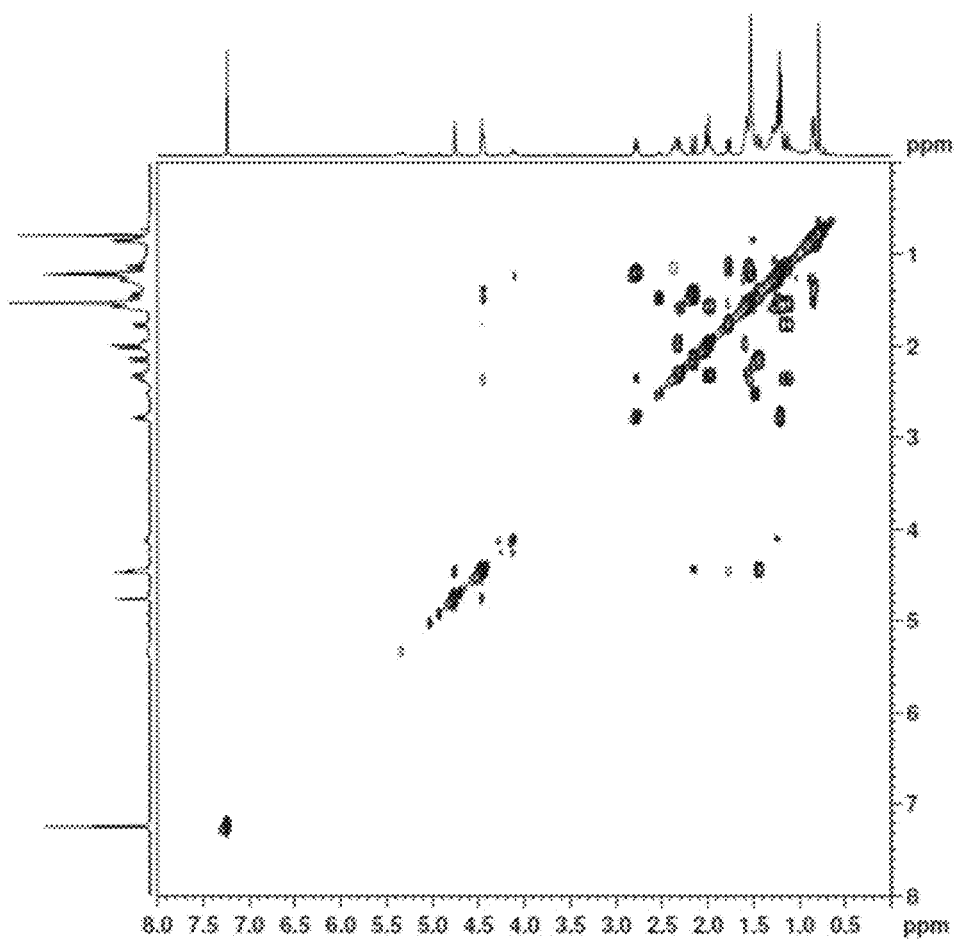
FIG. 3E shows the COSY spectrum for the compound of formula (I)
Figure 3F:
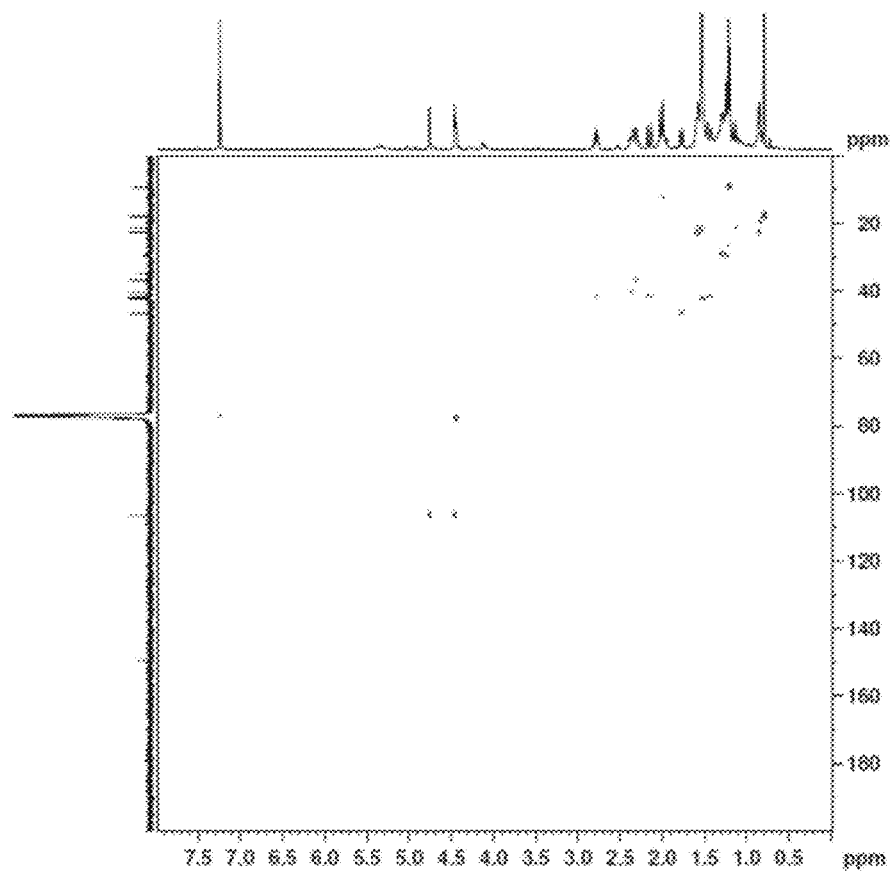
FIG. 3F shows the HSQC spectrum for the compound of formula (I)
Figure 3G:
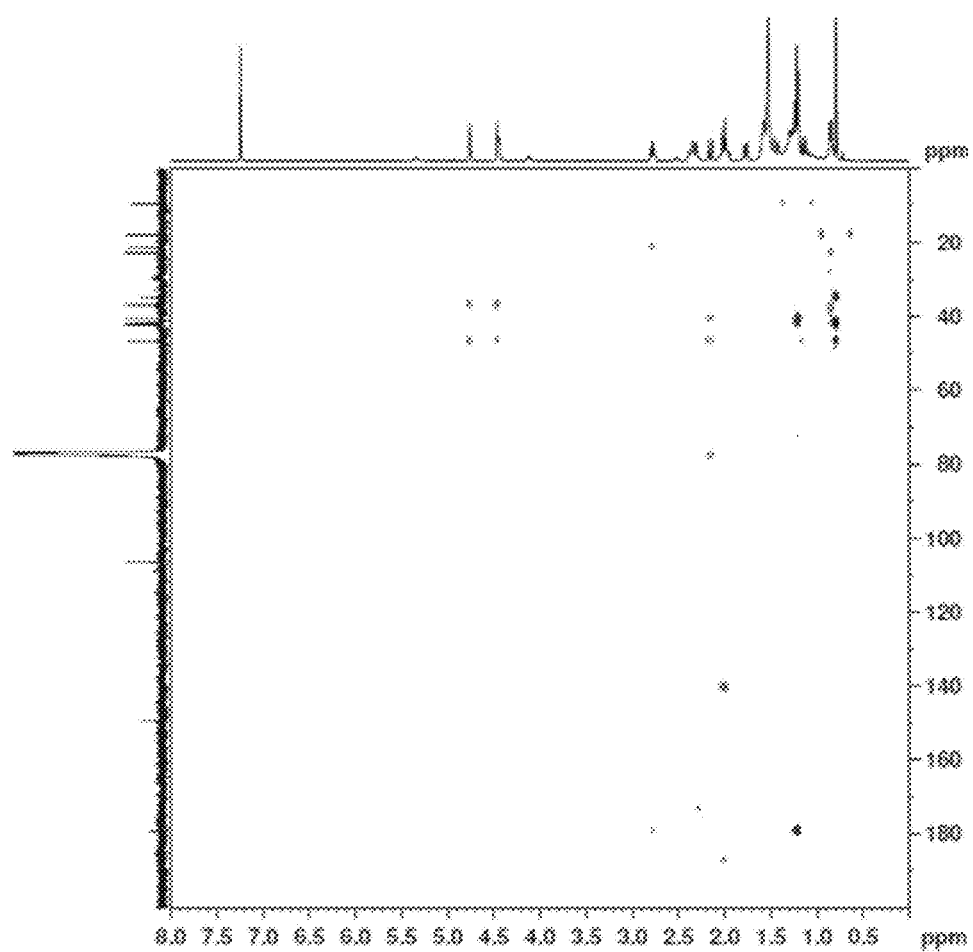
FIG. 3G shows the HMBC spectrum for the compound of formula (I)

Also, the above step (S4) comprises the following sub-steps:

(S41) carrying out an extraction of the ground biomass of step (S33) with 50%-100% and most preferably 70% food grade ethanol (EtOH) as an extraction solvent to produce an extract, with a ratio of the biomass to the 70% ethanol being 1:10 (w/v) and the extraction being performed in a 70° C. water bath for 30 minutes;

(S42) collecting at least one supernatant by centrifugation of the extract of step (S41) at 4800 rpm for 10 min After step (S42), the sesquiterpenoid compound of formula (I) can be isolated from the supernatant by column chromatography, such as utilizing a high performance liquid chromatography (HPLC) system equipped with a Luna 5 m C18 column (Phenomenex, U.S.). The elution is performed with $H_2O$ and MeCN. FIG. 2 is a flowchart illustrating isolation of the compound of formula (I) from a supernatant of the S. involucrate extract using column chromatography. As shown in FIG. 2, 16 ingredients (A-P) are obtained in step (S5). Among these, ingredient D is a sesquiterpenoid derivative, named compound of formula (I). To obtain the purified dry powder of the compound of formula (I), which is stored at room temperature and in the dark, the fraction containing the compound is concentrated using a rotary evaporator till the solvent is removed.

Identification the Compound of Formula (I)

The NMR spectroscopy (Nuclear Magnetic Resonance spectroscopy) is exploited to analyze the types of functional groups and the atomic bonding within the molecule of the compound of formula (I). The NMR spectra used for analysis include a $^1$H-NMR spectrum, a $^{13}$C-NMR spectrum, a DEPT (Distortionless Enhancement by Polarization Transfer) spectrum, a NOESY (Nuclear Overhauser Effect Spectroscopy) spectrum, a COSY (Correlation Spectroscopy) spectrum, a HSQC (Heteronuclear Single-Quantum Correlation Spectroscopy) spectrum, and a HMBC (Heteronuclear Multiple Bond Correlation) spectrum.

FIG. 3A to FIG. 3G show the $^1$H-NMR spectrum, the $^{13}$C-NMR spectrum, the DEPT spectrum, the NOESY spectrum, the COSY spectrum, the HSQC spectrum, and the HMBC spectrum for the compound of formula (I), respectively. According to these spectra, the molecular structure of the compound of formula (I) is determined.

The inhibitory effect of the compound of formula (I) on melanogenesis is validated by the following experiments. The promoting effects of the compound of formula (I) on collagen production and wound healing are also described.

EXAMPLE 1

Culture of Human Dermal Fibroblasts

Human dermal fibroblasts (CCD-966SK cells, former ATCC CRL-1881), a type of adherent skin cells, were cultured in minimum essential medium supplemented with 10% (v/v) fetal bovine serum (FBS), 0.37% (w/v) sodium bicarbonate, 0.1 mM non-essential amino acid solution (NEAA), 1 mM sodium pyruvate, 0.03% (w/v) L-glutamate, 100 units/ml penicillin and 100 μg/ml streptomycin at 37° C. under humidified atmosphere (relative humidity of 80%) containing 5% $CO_2$. During the culture, the medium was renewed every two days. When the cultured cells reached confluence and formed a monolayer, which was examined by an inverted microscope, a subculture was carried out.

EXAMPLE 2

Inhibition of MMP-9 Gene Expression and Enhancement of Collagen Secretion

Matrix metalloproteinase 9 (MMP-9) is a member of the matrix metalloproteinase (MMPs) family which involves in the breakdown and remodeling of extracellular matrix. Currently twenty-eight MMPs have been identified, among which are collagenases, gelatinases, stromelysins, matrilysins, and membrane type-MMPs. MMP-9 is classified as a gelatinase.

The extracellular matrix consists essentially of four components, namely collagens, elastin, glycoproteins, and proteoglycans. The proportion of each of the components in different tissues or organs varies. It is well-known that poor support of skin by collagen results in laxity and reduced elasticity of skin. The factors that affect collagen content of skin include MMPs levels. MMPs overexpression is stimulated by UV-A radiation or inflammation. Under these conditions, MMPs degrade almost all components of the extracellular matrix and break down proteins in the connective tissue, wherein collagen of the extracellular matrix is degraded and destroyed by MMP-9.

Therefore, the inventors of the present application studied the inhibitory effect of the compound of formula (I) on MMP-9 gene expression in EXAMPLE 2. The following five groups were compared in this example:

(1) Control group (CTL group): incubating a culture of human dermal fibroblasts for a predetermined time;

(2) One dose-24 hours group (1X-24 group): adding one dose of the compound of the present invention to a culture of human dermal fibroblasts and then examining the culture after an incubation of 24 hours, wherein the term "one dose" refers to 8.75 ng/mL of the compound of formula (I) in dimethyl sulfoxide (DMSO);

(3) One dose-48 hours group (1X-48 group): adding one dose of the compound of the present invention to a culture of human dermal fibroblasts and then examining the culture after an incubation of 48 hours;

(4) Double dose-24 hours group (2X-24 group): adding a double dose of the compound of the present invention to a culture of human dermal fibroblasts and then examining the culture after an incubation of 24 hours, wherein the term "double dose" refers to 17.5 ng/mL of the compound of formula (I); and (5) Double dose-48 hours group (2X-48 group): adding a double dose of the compound of the present invention to a culture of human dermal fibroblasts and then examining the culture after an incubation of 48 hours.

Figure 4:
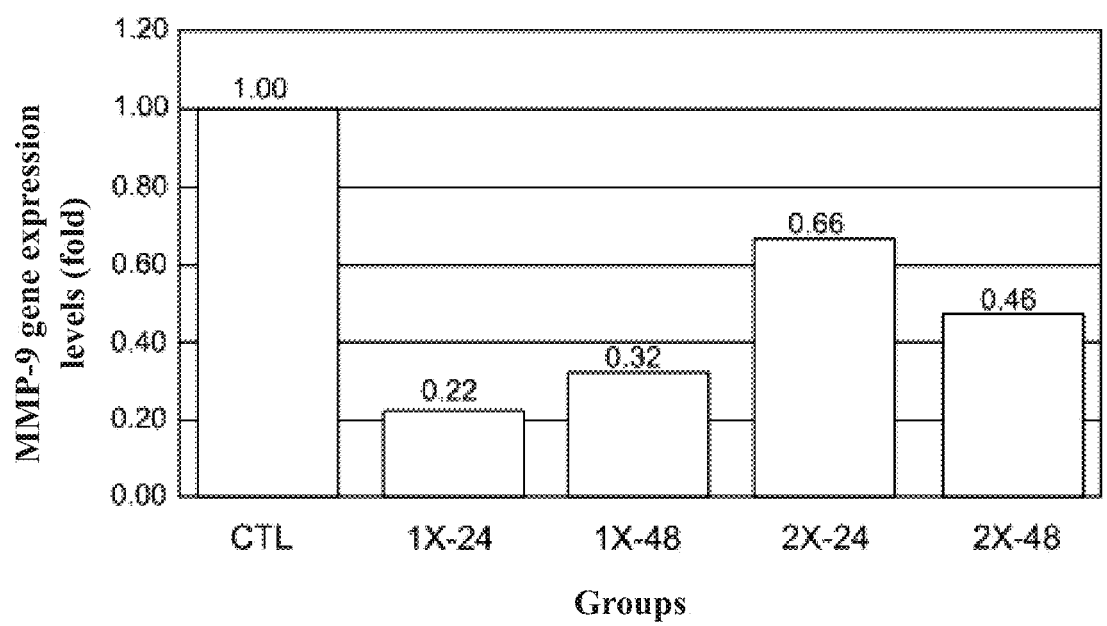
FIG. 4 shows MMP-9 gene expression levels in human dermal fibroblasts.

In EXAMPLE 2, RT-PCR (real-time polymerase chain reaction, ABI StepOnePlus™ System) was applied to monitor alterations of MMP-9 gene expression levels in human dermal fibroblasts upon addition of the compound of the present invention. The fold change of the MMP-9 gene expression levels was derived using the formula $2^{-\Delta\Delta Ct}$ with Ct referring to the threshold cycle number. FIG. 4 shows MMP-9 gene expression levels for each of the five groups, with the output being expressed as the fold-change of expression levels. According to FIG. 4, when compared with the CTL group, the 1X-24 group exhibited inhibition of MMP-9 gene expression by about 80%, which produced the greatest inhibitory effect. Besides, it is concluded that the compound at a concentration between 8 ng/ml and 18 ng/ml reduces MMP-9 gene expression in human dermal fibroblasts by an average of over 50%, such as a 58.5% reduction in this embodiment.

Figure 5:
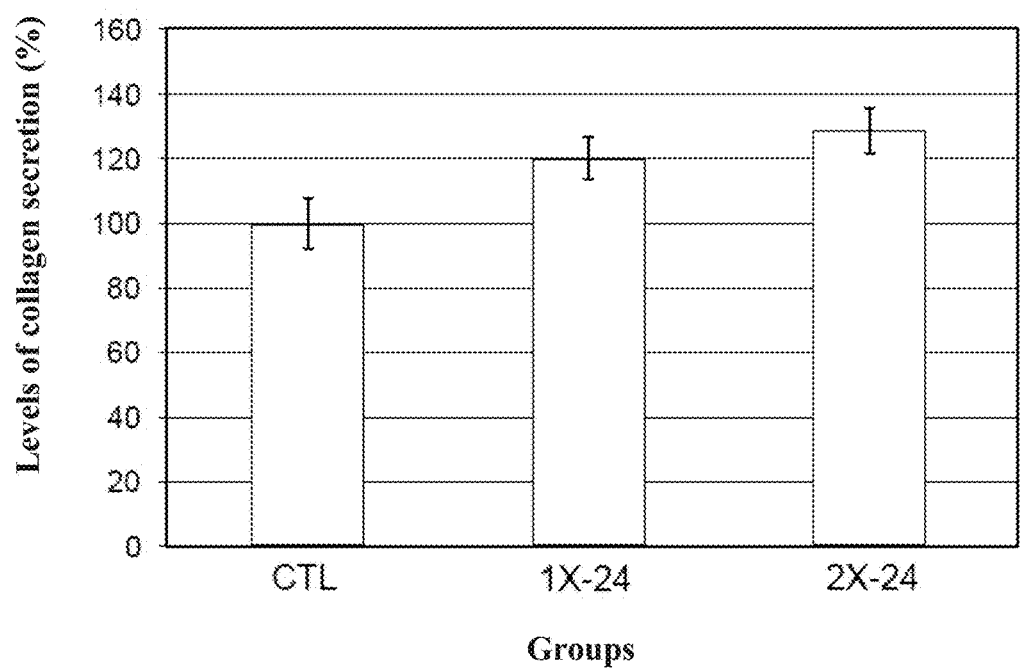
FIG. 5 shows levels of collagen secretion in human dermal fibroblasts.

In addition, a collagen secretion assay was performed to examine change of collagen content in cultures of human dermal fibroblasts upon addition of the compound of the present invention. The measurement of collagen content was followed the manufacturer's instruction (Sircol™ Collagen Assay, Biocolor, U.K.) and was based on detecting the absorbance of the collagen-binding dye at 555 nm FIG. 5 shows levels of collagen secretion for each group, with the value for each group being normalized to that for the CTL group. According to FIG. 5, when compared with the CTL group, the 1X-24 group exhibited a 20% increase in collagen secretion by human dermal fibroblasts. Also, when compared with the CTL group, the 2X-24 group showed a 30% increase in collagen secretion. Thus, it is concluded that the compound at a concentration between 8 ng/ml and 18 ng/ml causes an increase of at least 20% in collagen secretion by human dermal fibroblasts.

EXAMPLE 3

Inhibition of MITF Gene Expression and Melanin Formation

Melanogenesis is a complicated biosynthetic process, mainly an enzymatic reaction catalyzed by tyrosinase in melanocytes. A lot of genes are involved in the regulation of this process. Among them, the gene of microphthalmia-associated transcription factor (MITF) plays a critical role. MITF is found in melanocytes. It regulates melanin synthesis by enhancing the activity of tyrosinase. Therefore, inhibition of MITF gene expression results in lowered tyrosinase activity and thus inhibited melanogenesis, leading to skin whitening.

Therefore, the inventors of the present application studied the inhibitory effect of the compound of formula (I) on MITF gene expression in EXAMPLE 3. The following five groups were compared in this example:
  (1) Control group (CTL group): incubating a culture of human dermal fibroblasts for a predetermined time;
  (2) One dose-24 hours group (1X-24 group): adding one dose of the compound of the present invention to a culture of human dermal fibroblasts and then examining the culture after an incubation of 24 hours, wherein the term "one dose" refers to 8.75 ng/mL of the compound of formula (I) in DMSO;
  (3) One dose-48 hours group (1X-48 group): adding one dose of the compound of the present invention to a culture of human dermal fibroblasts and then examining the culture after an incubation of 48 hours;
  (4) Double dose-24 hours group (2X-24 group): adding a double dose of the compound of the present invention to a culture of human dermal fibroblasts and then examining the culture after an incubation of 24 hours, wherein the term "double dose" refers to 17.5 ng/mL of the compound of formula (I); and
  (5) Double dose-48 hours group (2X-48 group): adding a double dose of the compound of the present invention to a culture of human dermal fibroblasts and then examining the culture after an incubation of 48 hours.

Figure 6:
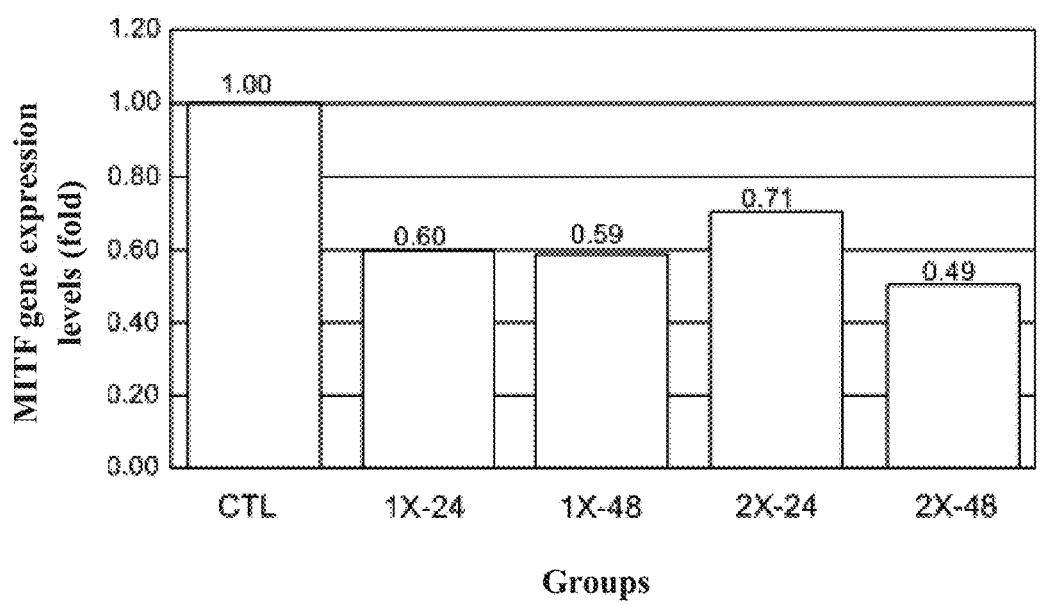
FIG. 6 shows MITF gene expression levels in human dermal fibroblasts.

Similar to EXAMPLE 2, RT-PCR was also applied to monitor alterations of MITF gene expression levels in human dermal fibroblasts upon addition of the compound of the present invention. FIG. 6 shows MITF gene expression levels for each of the five groups, with the output being expressed as the fold-change of expression levels. According to FIG. 6, when compared with the CTL group, the 2X-48 group exhibited inhibition of MITF gene expression by about 50%, which produced the greatest inhibitory effect. Besides, it is concluded that the compound at a concentration between 8 ng/ml and 18 ng/ml reduces MITF gene expression in human dermal fibroblasts by an average of over 40%.

Figure 7:
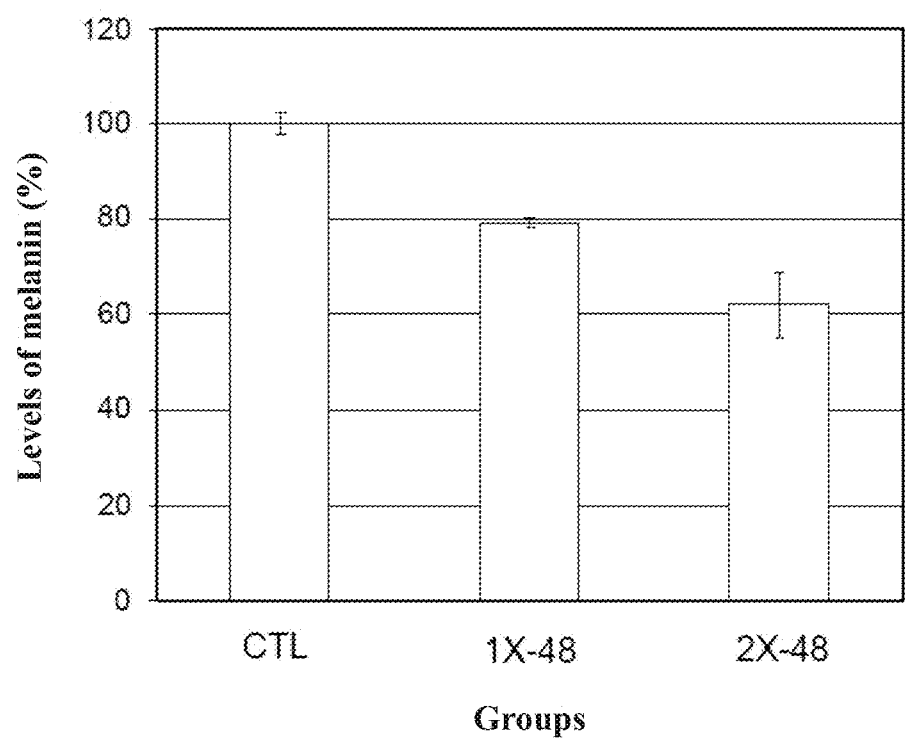
FIG. 7 shows levels of melanin in mouse melanoma cells.

In addition, a melanin quantification assay was performed to examine the change of melanin content in mouse melanoma cell line B16F10 (ATCC CRL-6475) upon addition of the compound of the present invention. The treatment of the cells was the same as described above. The measurement of melanin content was carried out by collecting the precipitates of B16F10 cell lysates (freeze-thaw), mixing the precipitates with 1N NaOH at 60° C. for 1 hour, and detecting the absorbance of the mixture at 405 nm FIG. 7 shows levels of melanin for each group, with the value for each group being normalized to that for the CTL group. According to FIG. 7, when compared with the CTL group, the 1X-48 group exhibited a 20% decreased melanin content in mouse melanoma cells. Also, when compared with the CTL group, the 2X-48 group exhibited a 40% decreased melanin content. Thus, it is concluded that the compound at a concentration between 8 ng/ml and 18 ng/ml causes a decrease of at least 20% in melanin formation in mouse melanoma cells.

EXAMPLE 4

Wound Healing of the Skin

Wound refers to tissue injuries to the skin when it is narrowly defined. Wound healing is a physiological process that is complex and dynamic, and it is related to cooperation between multiple cells and tissues for wound repair. The mechanism underlying wound healing of human skin can be divided into the following phases: blood clotting, inflammation, proliferation, and maturation. In the phase of proliferation, fibroblasts proliferate to form fibrocytes and produce collagen. During maturation, newly formed collagens replace the old ones to achieve collagen remodeling, which leads to the normal state of skin in both appearance and function.

Due to the importance of wound healing, the inventors of the present application studied the promoting effect of the compound of formula (I) on wound healing of skin in EXAMPLE 4. The following four groups were compared in this example:
  (1) Control group (CTL group): creating an incised wound area in a culture of human dermal fibroblasts and then incubating and examining the culture for 18 hours;
  (2) One dose-18 hours group (1X-18 group): creating an incised wound area in a culture of human dermal fibroblasts and adding one dose of the compound of the present invention to the culture; and then examining changes in the wound area of human dermal fibroblasts after an incubation of 18 hours, wherein the term "one dose" refers to 8.75 ng/mL of the compound of formula (I) in DMSO;
  (3) Double dose-18 hours group (2X-18 group): creating an incised wound area in a culture of human dermal fibroblasts and adding one dose of the compound of the present invention to the culture; and then examining changes in the wound area of human dermal fibroblasts after an incubation of 18 hours, wherein the term "double dose" refers to 17.5 ng/mL of the compound of formula (I); and (4) Fourfold dose-18 hours group (4X-18 group): creating an incised wound area in a culture of human dermal fibroblasts and adding one dose of the compound of the present invention to the culture; and then examining changes in the wound area of human dermal fibroblasts after an incubation of 18 hours, wherein the term "fourfold dose" refers to 35 ng/mL of the compound of formula (I).

Figure 8:
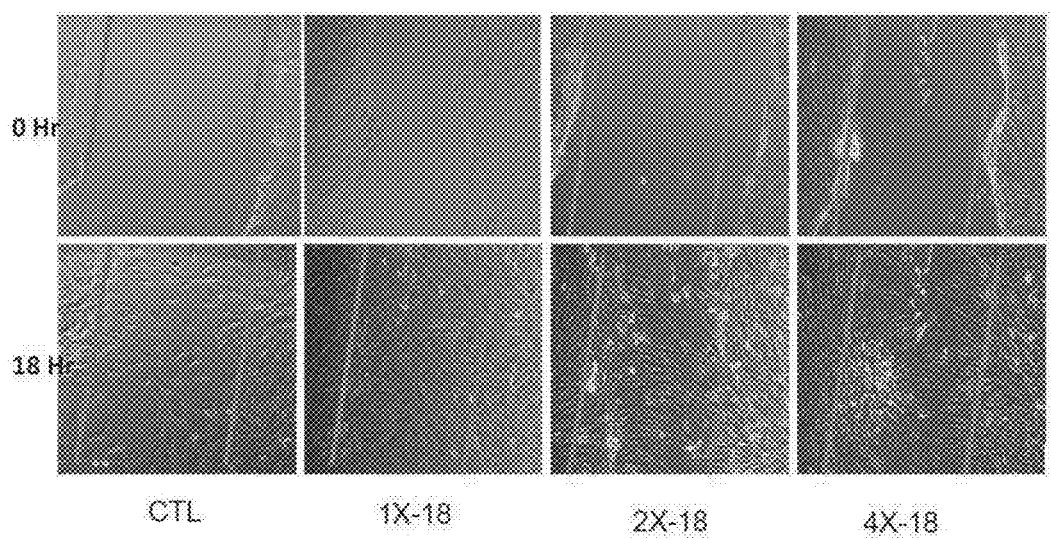
FIG. 8 shows micrographs (100×) of human dermal fibroblasts.

FIG. 8 shows micrographs (100×) of human dermal fibroblasts for each group. According to FIG. 8, a constant number of fibrocytes (about 1-2×10$^5$ cells) were produced in each of the CTL, 1X-18, 2X-18, and 4X-18 groups to repair and close the wound at 18 hours after wounding. However, it was noted that the 1X-18, 2X-18, and 4X-18 groups exhibited a significantly higher degree of repair/closure in the wound area, when compared with the CTL group.

Figure 9:
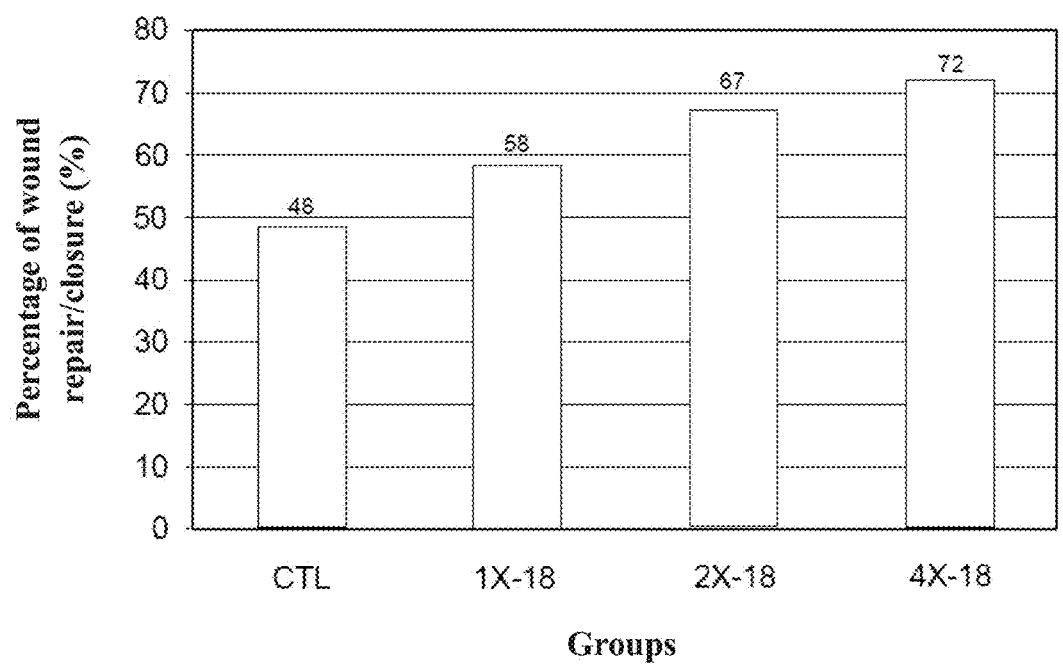
FIG. 9 shows the percentage of wound repair/closure in a wound area of human dermal fibroblasts.

In addition, a percentage of wound repair/closure in the wound area of human dermal fibroblasts was determined for the above four groups by analyzing the surface area change of the wound area in FIG. 8 using the software ImageJ. FIG. 9 shows the percentage of wound repair/closure in the wound area for each group. According to statistical data shown in FIG. 9, the percentage of wound repair/closure for the 1X-18 group was 1.21 fold higher than that of the CTL group; the percentage of wound repair/closure for the 2X-18 group was 1.4 fold higher than that of the CTL group; and the percentage of wound repair/closure for the 4X-18 group was 1.5 fold higher than that of the CTL group. Thus, it is concluded that the compound at a concentration between 8 ng/ml and 18 ng/ml facilitates repair and closure of a wound area of human dermal fibroblasts.

In conclusion, the inventors comprehensively and explicitly disclose every aspect of compound of the present invention, including the preparation method thereof, the chemical structure, and effects of inhibiting melanogenesis and promoting collagen production and wound healing. All disclosure supports that the compound has the following characteristics and advantages.

First, the compound of present invention is distinguished from the tyrosinase inhibitor extracted from *Saussurea laniceps* or general melanogenesis inhibitors in that it not only inhibits melanogenesis but also promotes collagen production and wound healing. Particularly, the experiments show the high activities of the compound to inhibit MMP-9 gene expression and MITF gene expression in human dermal fibroblasts.

Secondly, due to the inhibitory effects of the compound of the present invention on MMP-9 and MITF gene expression, the compound can further enhance collagen production in human dermal fibroblasts and at the same time inhibit melanin formation in mouse melanoma cells.

Thirdly, because EXAMPLEs 1-4 have revealed that the compound of the present invention inhibits melanogenesis, promotes collagen production, and promotes wound healing, it is practicable to manufacture compositions comprising the compound of formula (I) and a pharmaceutically acceptable carrier for inhibiting melanogenesis, promoting collagen production, and promoting wound healing in the skin of a subject in need thereof. For example, the compositions can be suspensions, solutions, emulsions, ointments, lotions, creams, gels, capsules, and powders for skin whitening, anti-aging, and wound healing. The compositions can further comprise hydroquinone, salicylic acid, an alpha hydroxy acid, hyaluronic acid, etc. The compound is also reliable for development of methods for inhibiting melanogenesis, promoting collagen production, and promoting wound healing in the skin of a subject in need thereof. Subjects who suffer from hypermelanogenesis, collagen loss, and skin injuries can be treated by administration of the compound of the present invention, either topically or orally.

The present invention has been described with reference to the above preferred embodiments. However, it will be apparent to those skilled in the art that modifications and changes in form and detail may be made without departing from the scope of the present invention defined by the appended claims.

What is claimed is:

1. A method for inhibiting melanogenesis, promoting collagen production, and promoting wound healing in the skin of a subject in need thereof, comprising administering to the subject an effective amount of a compound of formula (I):

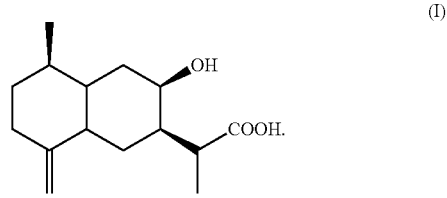 [SMILES: C=C1CC[C@@H](C)C2C[C@@H](O)[C@@H](C(C)C(=O)O)CC12]

2. The method of claim 1, wherein the compound inhibits gene expression of microphthalmia-associated transcription factor (MITF) in human dermal fibroblasts.

3. The method of claim 1, wherein the compound inhibits gene expression of matrix metalloproteinase 9 (MMP-9) in human dermal fibroblasts.

4. The method of claim 1, wherein the compound facilitates repair and closure of a wound area of human dermal fibroblasts.

5. The method of claim 1, wherein the compound is at a concentration of between 8 ng/ml and 18 ng/ml.

* * * * *